US011324967B2

(12) United States Patent
Heibel

(10) Patent No.: US 11,324,967 B2
(45) Date of Patent: May 10, 2022

(54) THERAPEUTIC ELECTRON RADIATOR FOR CANCER TREATMENT

(71) Applicant: Westinghouse Electric Company LLC, Cranberry Township, PA (US)

(72) Inventor: Michael D. Heibel, Harrison City, PA (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 437 days.

(21) Appl. No.: 16/274,808

(22) Filed: Feb. 13, 2019

(65) Prior Publication Data
US 2019/0255353 A1      Aug. 22, 2019

Related U.S. Application Data

(60) Provisional application No. 62/631,734, filed on Feb. 17, 2018.

(51) Int. Cl.
*A61N 5/10*          (2006.01)
(52) U.S. Cl.
CPC ......... *A61N 5/1031* (2013.01); *A61N 5/1027* (2013.01); *A61N 5/1048* (2013.01); *A61N 5/1067* (2013.01); *A61N 5/1077* (2013.01); *A61N 2005/109* (2013.01); *A61N 2005/1089* (2013.01); *A61N 2005/1094* (2013.01)
(58) Field of Classification Search
CPC ...... A61N 5/1001; A61N 5/1014–1017; A61N 5/1027; A61N 2005/1089; A61N 2005/109; A61N 2005/1094; A61N 2005/1095
See application file for complete search history.

(56) References Cited

U.S. PATENT DOCUMENTS

| 6,107,102 A | * | 8/2000 | Ferrari ................... A61K 9/127 424/417 |
| 9,833,637 B2 | * | 12/2017 | Isham .................. A61N 5/1064 |
| 2002/0133220 A1 | | 9/2002 | Lundqvist |

(Continued)

FOREIGN PATENT DOCUMENTS

| EP | 1232771 A1 | 8/2002 |
| RU | 2606337 C1 | 10/2017 |

(Continued)

OTHER PUBLICATIONS

Haume, K., et al., "Gold nanoparticles for cancer radiotherapy: a review", Cancer Nano., 2016, vol. 7, No. 8, pp. 1-20.

(Continued)

*Primary Examiner* — Carrie R Dorna
(74) *Attorney, Agent, or Firm* — K&L Gates LLP

(57) ABSTRACT

A method that produces high energy charged particles that may be used to destroy cancer cells contained in cancerous tissues. The device uses electronic neutron generators to produce neutrons with energies that have a high probability to interact with a therapeutic source comprised of a reactive material with an outer layer of a material having a high atomic number such as Platinum or Gold. The reaction produces high energy electrons, and in some cases other charged particles with relatively short half-lives, which can destroy the cancerous cells, without seriously damaging the surrounding healthy tissue.

19 Claims, 2 Drawing Sheets

(56) References Cited

U.S. PATENT DOCUMENTS

| 2012/0330084 A1* | 12/2012 | Pantell | A61N 5/10 |
| | | | 600/1 |
| 2013/0066135 A1* | 3/2013 | Rosa | A61N 5/10 |
| | | | 600/1 |
| 2014/0181114 A1 | 6/2014 | Schuster et al. | |
| 2017/0108591 A1* | 4/2017 | Kuri | G01T 7/00 |
| 2017/0173364 A1* | 6/2017 | Hainfeld | A61N 5/10 |

FOREIGN PATENT DOCUMENTS

| WO | 0170336 A1 | 9/2001 |
| WO | 2005/107387 A2 | 11/2005 |
| WO | 2015/017034 A1 | 2/2015 |
| WO | 2019160931 A1 | 8/2019 |

OTHER PUBLICATIONS

Setua, S. et al., "Cisplatin-tethered gold nanospheres for multimodal chemo-radiotherapy of glioblastoma", Nanoscale, 2014, vol. 6, No. 8, pp. 10865-10873.
International Search Report and Written Opinion for PCT/US2019/017821, dated Jun. 4, 2019.
Jennings, et al., "Novel Compact Accelerator-Based Neutron and Gamma Sources for Future Detector Calibration", Snowmass 2013 White Paper, 2 pages.
International Search Report and Written Opinion for International PCT Application No. PCT/US2019/017821, dated Jun. 4, 2019.
Supplementary European Search Report counterpart European Application No. 19755216.9, dated Oct. 4, 2021.

* cited by examiner

THERAPEUTIC ELECTRON RADIATOR FOR CANCER TREATMENT

CROSS-REFERENCE TO RELATED APPLICATIONS

This application claims priority under 35 U.S.C. § 119(e) from: U.S. Provisional Patent Application No. 62/631,734, entitled THERAPEUTIC ELECTRON RADIATOR FOR CANCER TREATMENT, filed on Feb. 17, 2018. The contents of the aforesaid application is incorporated herein by reference in its entirety.

BACKGROUND

1. Field

This invention pertains generally to the treatment of cancer and, more particularly to the treatment of highly localized carcinoma cells.

2. Related Art

The treatment of highly localized carcinoma cells, such as tumors, in the human body using ionizing radiation has proven to be quite effective. However, the application of ionizing radiation to the body typically involves having the radiation pass through healthy tissue before it arrives at the intended target site. This results in damage to the healthy tissue. This limits the amount of damage that can be done to the tumor at one time, resulting in the need for multiple treatments and the accumulating adverse potential biological consequences and financial costs of the treatments. If the healthy cell damage repair does not keep up with the tumor growth rate and/or metastasis rate to allow for sufficient treatment, the victim is likely to perish from the consequences of the carcinoma. Accordingly, a new method of treatment is desired that will attack the cancerous tissue with a minimal effect on the surrounding healthy tissue.

Boron Neutron Capture Therapy (BNCT) has been explored as a possible answer to the foregoing need, however, to date it has been found to lack the therapeutic range of the emitted radiation to be effective. The problem to be solved then is how to take advantage of the neutron generation and application methodology of the Boron Neutron Capture Therapy and increase the therapeutic range of the emitted radiation.

SUMMARY OF THE INVENTION

This invention overcomes the detrimental effects of the radiation treatment of cancer by providing a method of treating localized carcinoma cells in a body of an animal that includes the step of positioning a therapeutic source that is substantially nonradioactive when not exposed to a neutron source below a given activity level, but becomes a source of highly ionizing but weakly penetrating radiation, comprising high energy electrons, when exposed to a neutron field at or above the given activity level, within the body in the vicinity of the carcinoma cells. Preferably, the positioning step surgically implants the therapeutic source material on the carcinoma cells. The therapeutic source is irradiated from outside the body with a neutron field at or above the given activity level for a prescribed period of time and the irradiation step is repeated at prescribed intervals. This invention focuses on the design and operation of the therapeutic source as the irradiation target to increase the energy and range of the emitted radiation.

In one preferred embodiment the device uses electronic neutron generators to produce neutrons that interact with Boron-10 to produce Helium and Lithium ions. The B-10 material is surrounded by a very thin layer of atoms with high atomic numbers, such as Platinum or Gold. The Helium and Lithium ions are born with large kinetic energies, and when they collide with the dense electron clouds in the surrounding layers of material, large numbers of high energy Compton and photoelectrical scattered electrons are created. The emitted electrons may be used to irradiate cancerous tissue adjacent to or surrounding the emitter package. The irradiation ceases when the electronic neutron generator system is turned off. The impact of the emitted electrons is further controlled by the application of electric and/or magnetic fields positioned to accelerate the emitted electrons into a penetration depth and/or preferred irradiation direction within the patient tissue.

In another embodiment this device uses electronic neutron generators to produce neutrons with energies that have a high probability to interact with a material like Hafnium to produce prompt neutron capture gamma radiation that is used to both directly irradiate cancer cells and to produce Compton and photoelectrical electrons that irradiate cancer cells. To accomplish this, the hafnium material is surrounded by a thin layer of atoms with high atomic numbers, such as Platinum or Gold. When Hafnium absorbs a neutron, it immediately releases a fairly high energy gamma photon. The gamma radiation primarily destroy the more radiation sensitive cancer cells within the range of the gamma photons. The resulting Hafnium isotope is generally not radioactive, so no further radiation is released unless the Hafnium daughter product then absorbs a neutron. In addition to the gamma photon damage, when the gamma radiation collides with the dense electron clouds in the surrounding layers of material, large numbers of high energy Compton and photoelectrical scattered electrons are created. The emitted electrons also irradiate cancerous tissue near to or surrounding the emitter package with a much higher probability of destroying the pernicious cells. The packages can be made in many shapes and sizes to allow them to be placed directly into or adjacent to cancerous tissue. Since the material is not radioactive unless it is being irradiated by neutrons, there is no personnel radiation exposure occurring while the material is being positioned. The irradiation ceases when the electronic neutron generator system is turned off. The impact of the emitted electrons is further controlled by the application of electric and/or magnetic fields positioned to accelerate the emitted electrons into a penetration depth and/or preferred irradiation direction within the patient tissue.

Preferably, the therapeutic source of highly ionizing, but weakly penetrating radiation is configured so it substantially only irradiates the carcinoma cells. To achieve that end a radiation shield material is formed on a side of the therapeutic source not facing the carcinoma cells. Preferably, the step of irradiating the therapeutic source includes the step of using an electric neutron generator, such as a Neutristor, to irradiate the therapeutic source. One such embodiment employs a plurality of electric neutron generators positioned around the body to irradiate the therapeutic source from different angles.

The method may also include the step of using a neutron moderating material between the electric neutron generator and the therapeutic source to adjust the neutron energy to optimize the highly ionizing, but weakly penetrating radiation produced by the therapeutic source. The neutron moderating material may be $D_2O$, C or other material having similar moderating properties. The neutron moderating material is placed outside the body between the electric neutron generator and the body.

In either embodiment the therapeutic source may be left within the body between treatments of treating the localized carcinoma cells, with the therapeutic source removed from the body once the treatments are complete. The therapeutic source may comprise one or more very thin disks or plates on the order of a micron thickness with a sufficient combined surface area to ensure the entire volume of localized carcinoma cells are affected by the highly ionizing but weakly penetrating radiation when one or more of the disks or plates are emplaced around the carcinoma cells and irradiated with the neutron field.

The method may also include the step of using a gamma spectrometer to monitor the intensity of gamma radiation emitted as a byproduct of the neutron radiation of the therapeutic source material and the charged particle production rate can be monitored while the neutron irradiation is occurring. The monitored intensity of the gamma radiation and neutron activity of the neutron field can be used to determine the radiation dose that has been applied to the body. The method may also control the intensity of the neutron field based on the monitored gamma intensity and the radiation dose.

BRIEF DESCRIPTION OF THE DRAWINGS

A further understanding of the invention can be gained from the following description of the preferred embodiments when read in conjunction with the accompanying drawings in which.

DESCRIPTION OF THE PREFERRED EMBODIMENTS

Figure 1:
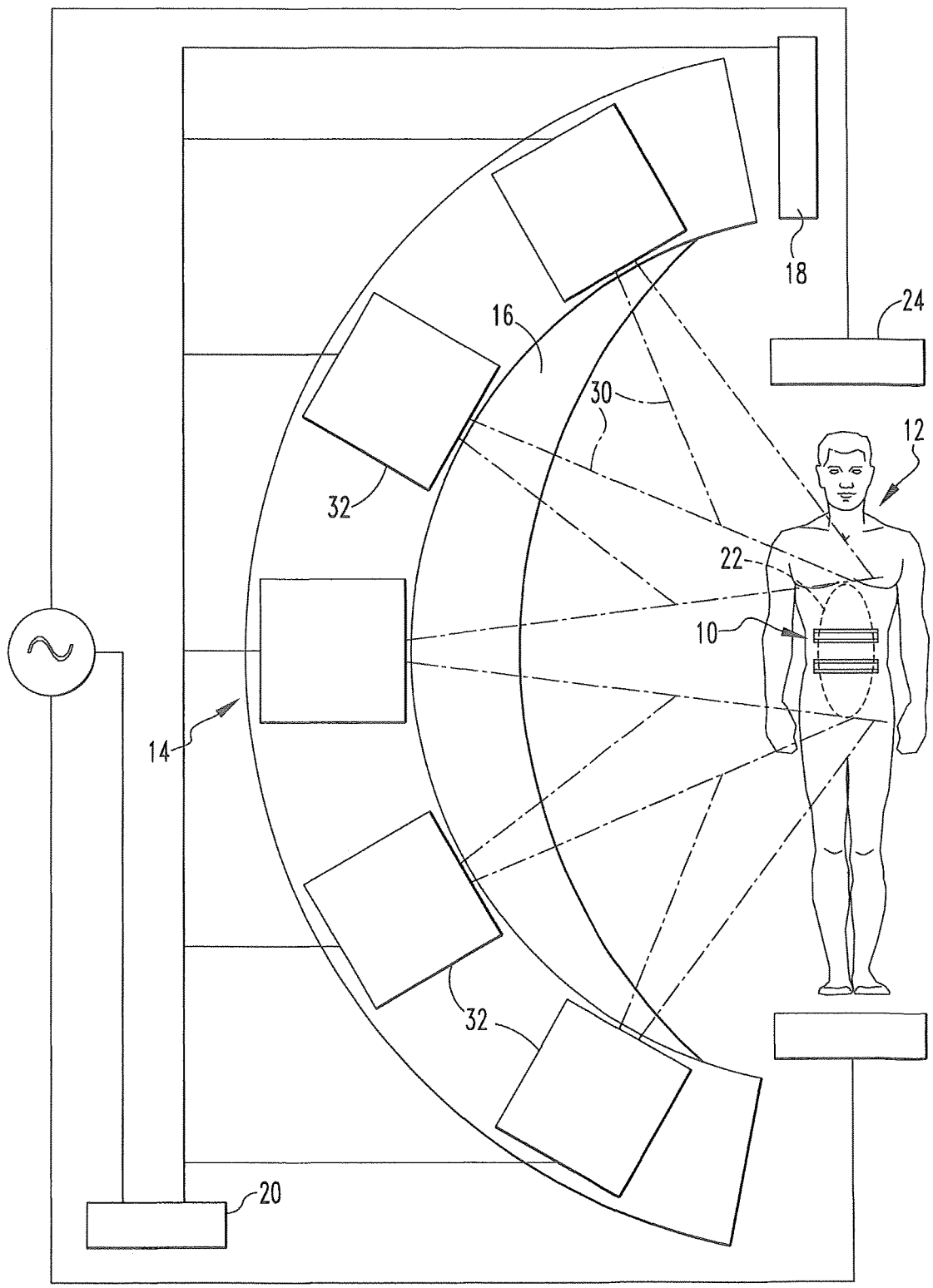
FIG. 1 is a schematic of the apparatus that may be employed to practice the method of this invention according to one embodiment of this invention.

The invention includes systems and methods for treating carcinoma cells that are localized in a body of an animal, including a subject, human, person or patient (which terms are using interchangeably herein), which include therapeutic and irradiation sources. The therapeutic source is positioned or implanted within the body of the patient and, more particularly, in the location or vicinity of the carcinoma cells. In certain embodiments, the therapeutic source is positioned on or adjacent to the carcinoma cells. The therapeutic source includes one or more devices that include disk(s) or plate(s) or needle(s) having a thickness of about one micron. The one or more disk(s) or plate(s) or needle(s) each or together have sufficient surface area to ensure that the entire volume of the localized carcinoma cells will be affected by emitted radiation. The therapeutic source should be composed or constructed of a material that produces high energy charged particles. Suitable materials are insoluble in water and non-toxic. The neutron reaction products of the material should also be non-toxic to the patient and have very short half-lives.

The therapeutic source comprises a first material that is substantially nonradioactive without neutron irradiation at a threshold level but becomes a source of highly ionizing and weakly penetrating radiation (particles) when exposed to a neutron field above the threshold level. The threshold level may be zero or a preset intensity level. This first material is attached on at least one side to a second material. The second material has a high atomic number. Optionally, the first material is attached on two sides to a second material. The therapeutic source or the irradiation target can be configured in any number of shapes, such as needles or disks, to allow a great deal of therapeutic flexibility.

In one embodiment the first material of the irradiation target comprises Boron-10; and the second material comprises a high atomic number such as Platinum or Gold. When B-10 absorbs a thermalized neutron, it splits into highly energetic Helium and Lithium ions. A significant fraction of these nuclei collides with the electron clouds surrounding the Platinum or Gold atoms. This results in the release of many Compton and photoelectrical scattered electrons in the MeV energy range. These electrons are much more penetrating than the He and Li ions that are the basis for the current BCNT methods. Since the range of the electrons produced is still very small relative to gamma radiation treatments, the damage to healthy tissue surrounding the cancerous area is minimized. The Boron Electron Radiator Target (BERT) can be configured in a number of shapes, such as needles or disks, to allow a great deal of therapeutic flexibility.

In another embodiment the first material of the irradiation target comprises Hafnium metal; and a second material is a high atomic number such as Platinum or Gold. When hafnium absorbs a neutron, it immediately releases gamma photons with an average energy of approximately 6 MeV. A significant fraction of these photons collides with the electron clouds surrounding the Platinum or Gold atoms. This results in the release of many Compton and photoelectrical scattered electrons in the multi-MeV energy range. Since the range of the electrons produced is still very small relative to gamma radiation treatments, the damage to healthy tissue surrounding the cancerous area is minimized. The Pulsed Neutron Capture Gamma (PNCG) Radiator Target can be configured in a number of shapes, such as needles or disks, to allow a great deal of therapeutic flexibility.

The therapeutic source material, herein interchangeably referred to as the irradiation target, is shaped using a number of commercially available fabrication techniques and, preferably, has a shielding over at least one side of the source material facing away from the carcinoma that is substantially transparent to neutrons, but shields at least some of the highly ionizing particles from the healthy tissue surrounding the carcinoma. Suitable materials include a light metal like aluminum, and like materials that have similar shielding properties. The presence of the therapeutic shield and configuration/position of the therapeutic source contributes to irradiating only the carcinoma cells, and not irradiating healthy cells.

The invention also includes an array of miniature electrically powered fast neutron generators. The neutron generators optionally have a configuration similar to the "Neutristor" design developed by Sandia National Laboratory and described in a Snowmass 2013 White Paper entitled *Novel Compact Accelerator Based Neutron and Gamma Sources for Future Detector Calibration*, G. Jennings, C. Sanzeni, D. R. Winn, Fairfield University, Fairfield Conn. 06824, and can be used to irradiate the therapeutic source with a neutron field once the source is implanted in the patient. Ideally, the array is configured as necessary to provide a neutron intensity at the source position sufficient to maximize the neutron reaction rate without providing too much neutron exposure to other parts of the subject's body. Ideally, the array is geometrically configured to provide neutrons incident on the carcinoma at different angles to provide the maximum number of sufficiently thermalized neutrons from each generator in the array to reach the target location. This can be accomplished through a combination of neutron source array geometry and variations in the thickness of the neutron moderating material in the neutron moderator placed between the neutron array and the irradiation target. The calculations required to establish the optimum conditions can be performed by those skilled in the art using a number of different commercially available neutron transport calculation products, such as MCNP available from Los Alamos National Laboratory.

Optionally, a neutron moderator is provided that is geometrically configured, i.e., configured to mate the tissue being irradiated, includes a sufficient amount of a material like $D_2O$ or C to be placed between each neutron generator device and the therapeutic source or irradiation target and is independently adjusted to achieve the goal of providing the maximum number of neutrons with the optimum energy for charged particle generation by neutron reactions with the therapeutic source or irradiation target.

Desirably, a gamma spectrometer is provided that measures the intensity of the gamma radiation emitted by the target isotope created in the neutron reaction so the charged particle production rate can be monitored while the neutron irradiation is occurring. This can be accomplished using a number of commercially available devices.

A computational control system uses the measured gamma activity and/or the activity status of the neutron generators to determine radiation dose that has been applied to the patient relative to a dose target. The control system has the ability to increase or decrease the intensity of the neutrons provided by any or all of the neutron generators in the array based on gamma intensity and measured dose measurements.

The dose of neutron irradiation applied can also be adjusted via neutron generator power according to the desired therapeutic effect in combination with the geometry of neutron generators and neutron moderator. Likewise, the duration of irradiation can also be adjusted.

FIG. 1 shows a system for treating highly localized carcinoma cells in accordance with this invention. The system employs one or more therapeutic source material 10 (FIG. 2) with sufficient surface area to ensure that the entire volume of the localized carcinoma cells will be affected by the radiation emitted when exposed to a neutron field. In one embodiment, the therapeutic source material 10 comprises very thin (e.g., micron thickness) disks or plates with sufficient surface area to ensure that the entire volume of the localized carcinoma cells will be affected by the radiation emitted when one or more of the devices are implanted within a patient 12 proximate to, and preferably adjacent the tumor tissue 22 and irradiated with neutrons 30 from electronic neutron generators device 14. The therapeutic source material 10 used should be one that produces high energy charged particles. The therapeutic source material 10 must be insoluble in water and non-toxic. The neutron reaction products of the therapeutic source material 10 should also be non-toxic to the subject and have very short half-lives.

FIG. 1 also provides a schematic illustration of an embodiment of the design of the irradiation target 10, also referred to as the therapeutic source material 10. The figure shows a representation of the neutron generator device 14 comprising an array of neutron generators 32 that can be configured to provide the neutron energy and dose distribution at the site of the irradiation target 10 through a combination of distance from the patient 12 and neutron moderator 16 (typically made of a flexible moderating material), such as a configurable mass of a highly hydrogenous material or various amounts of deuterium contained in a specially configured plastic container, i.e., configured to match the contour of the tumor tissue 22 being irradiated, positioned between the neutron generator device 14 and the patient 12.

Figure 2:
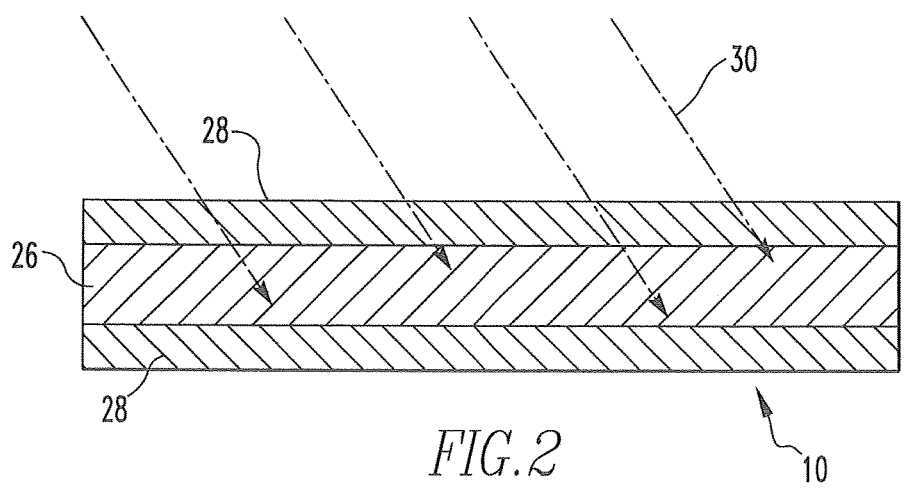
FIG. 2 is an illustration of a therapeutic source material according to one embodiment of this invention.

As shown in FIG. 2, the therapeutic source material 10 comprises a first material 26 that is substantially nonradioactive without neutron irradiation at a threshold level but becomes a source of highly ionizing and weakly penetrating radiation (particles) when exposed to a neutron field above the threshold level. The threshold level may be zero or a preset intensity level. The first material 26 is attached on at least one side to a second material 28. The second material 28 has a high atomic number. Optionally, the first material 26 is attached on two sides to a second material 28 (FIG. 2). The therapeutic source material 10 or the irradiation target 10 can be configured in any number of shapes, such as needles or disks, to allow a great deal of therapeutic flexibility.

In one embodiment the first material 26 of the irradiation target 10 comprises a thin layer of $B_4C$ composed of mostly Boron-10 (1 µm) sandwiched between very thin (1 µm thick) sheets of a second material 28 with a high atomic number such as Platinum or Gold.

In another embodiment the first material 26 of the irradiation target 10 comprises a thin layer of natural Hafnium metal (1 mm) sandwiched between very thin (1 mm thick) sheets of a material 28 with a high atomic number such as Platinum or Gold.

The therapeutic source material 10, i.e., the irradiation target 10, to be inserted for irradiation can be shaped using a number of commercially available fabrication techniques and, preferably, has a shielding over at least one side of the source material facing away from the carcinoma that is substantially transparent to neutrons, but shields at least some of the highly ionizing particles from the healthy tissue surrounding the carcinoma. Such a shield may be constructed out of a light metal, optionally aluminum.

An array of miniature electrically powered fast neutron generators 32 can be used to irradiate the therapeutic source material 10 with a neutron field once the source material 10 is implanted in the patient. Ideally, the array is configured as necessary to provide a neutron intensity at the source position sufficient to maximize the neutron reaction rate without providing too much neutron exposure to other parts of the subject's body. Ideally, the array is geometrically configured to provide neutrons incidents on the carcinoma at different angles to provide the maximum number of sufficiently thermalized neutrons 30 from each generator in the array to reach the target location. This can be accomplished through a combination of neutron source array geometry and variations in the thickness of the neutron moderating material in the neutron moderator 16 placed between the neutron array and the irradiation target 10.

Preferably, a neutron moderator 16 is provided that is geometrically configured, i.e., configured to mate the tissue being irradiated, includes a sufficient amount of a material like $D_2O$ or C to be placed between each neutron generator device 14 and the therapeutic source material or irradiation target 10 and is independently adjusted to achieve the goal of providing the maximum number of neutrons 30 with the optimum energy for charged particle generation by neutron reactions with the therapeutic source material or irradiation target 10.

A gamma spectrometer 18 is provided that measures the intensity of the gamma radiation emitted by the target isotope created in the neutron reaction so the charged particle production rate can be monitored while the neutron irradiation is occurring. This can be accomplished using a number of commercially available devices.

A computational control system 20 uses the measured gamma activity and the activity status of the neutron generators 32 to determine radiation dose that has been applied to the patient 12 relative to a dose target. The control system 20 has the ability to increase or decrease the intensity of the neutrons provided by any or all of the neutron generators 32 in the array based on gamma intensity and measured dose measurements.

The dose of neutron irradiation applied can also be adjusted via neutron generator power according to the desired therapeutic effect in combination with the geometry of neutron generators 32 and neutron moderator 16. Likewise, the duration of irradiation can also be adjusted.

Optionally, the external electric and/or magnetic field can be manipulated through electric field plate 24 to change the kinetic energy and primary direction of movement of the electrons emitted from the irradiator target 10 to better control the applied dose to the patient. As an example, application of an oscillating electric field will allow the radiated electrons to be accelerated beyond, or suppressed from, the range dictated by the kinetic energy imparted by the gamma photon collisions with the Gold or Platinum electrons. Application of an external magnetic field could be used to concentrate the emitted electron density nearer to or further from the emitter element.

The method and system for treating carcinoma described herein is different from other types of radiation treatments in that it relies on creating and implanting a non-radioactive target in or around a tumor versus the injection of a compound that provides a limited amount of therapeutic treatment deposition in the desired area. The ability this system provides to perform neutron activation of initially non-radioactive materials in a hospital environment maximizes the benefits of charged particle cancer treatment and minimizes the unwanted expense and radiation exposure to the patient and caregivers. This approach allows very precise and efficient cancer killing to occur. Additionally, the target source can be left in position without increasing the whole body radiation dose to the patient, until the tumor is completely dead. Multiple irradiations can occur with relative ease. The use of the neutristor neutron generator provides the ability to perform the treatments in a hospital setting instead of a reactor or very large neutron source location. This greatly reduces treatment costs (or greatly increases treatment profitability) relative to existing radiation treatment methods.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

What is claimed is:
1. A method of treating localized carcinoma cells in a body of an animal comprising the steps of:
  positioning a therapeutic source within the body in the vicinity of the carcinoma cells, the therapeutic source comprising
    a first material comprising Boron-10 or hafnium; and
    an outer layer of a second material comprising platinum, gold, or a combination thereof;
  wherein the therapeutic source is substantially nonradioactive when not exposed to a neutron field, but becomes a source of ionizing radiation when exposed to the neutron field;
  irradiating the therapeutic source from outside the body with the neutron field; and
  repeating the irradiating step at prescribed intervals.

2. The method of treating localized carcinoma cells of claim 1 wherein the therapeutic source of ionizing radiation is configured so it substantially only irradiates the carcinoma cells.

3. The method of treating localized carcinoma cells of claim 2 wherein a radiation shield material that shields at least some of the ionizing radiation, but is substantially transparent to neutrons, is formed on a side of the therapeutic source not facing the carcinoma cells.

4. The method of treating localized carcinoma cells of claim 3 wherein the radiation shield material comprises aluminum.

5. The method of treating localized carcinoma cells of claim 1 wherein the positioning step includes the step of surgically implanting the therapeutic source material approximately on the carcinoma cells.

6. The method of treating localized carcinoma cells of claim 1 wherein the step of irradiating the therapeutic source includes the step of using an electric neutron generator device to irradiate the therapeutic source.

7. The method of treating localized carcinoma cells of claim 6 wherein the electric neutron generator device includes a plurality of electric neutron generators positioned around the body to irradiate the therapeutic source from different angles.

8. The method of treating localized carcinoma cells of claim 6 further comprising the step of using a neutron moderating material between the electric neutron generator and the therapeutic source to adjust the neutron energy to optimize the ionizing, radiation produced by the therapeutic source.

9. The method of treating localized carcinoma cells of claim 8 wherein the neutron moderating material comprises $D_2O$ or C.

10. The method of treating localized carcinoma cells of claim 8 wherein the step of using the neutron moderating material includes the step of placing the neutron moderating material outside the body.

11. The method of treating localized carcinoma cells of claim 1 further comprising the step of leaving the therapeutic source within the body between treatments of treating the localized carcinoma cells.

12. The method of treating localized carcinoma cells of claim 11 further comprising the step of removing the therapeutic source from the body once treatment of the localized carcinoma cells is completed.

13. The method of treating localized carcinoma cells of claim 1 wherein the therapeutic source comprises one or more very thin disks or plates in the order of a micron's thickness with a sufficient combined surface area to ensure the entire volume of localized carcinoma cells is affected by the ionizing radiation when one or more of the disks or plates are emplaced around the carcinoma cells and irradiated with the neutron field.

14. The method of treating localized carcinoma cells of claim 1 further comprising the step of using a gamma spectrometer to monitor an intensity of gamma radiation emitted by a product of neutron radiation of the therapeutic source material, and to monitor a charged particle production rate, while the neutron irradiation is occurring.

15. The method of treating localized carcinoma cells of claim 14 further comprising the step of using the intensity of the gamma radiation and the charged particle production rate to determine a radiation dose that has been applied to the body.

16. The method of treating localized carcinoma cells of claim 15 further comprising the step of controlling an intensity of the neutron irradiation based on the intensity of gamma radiation and the radiation dose.

17. The method of treating localized carcinoma cells of claim 1 wherein the first material comprises primarily Boron-10.

18. The method of treating localized carcinoma cells of claim 1 wherein the first material comprises $B_4C$.

19. The method of treating localized carcinoma cells of claim 1 wherein the first material comprises Hafnium.

\* \* \* \* \*